United States Patent
Boukari

(10) Patent No.: US 11,216,825 B2
(45) Date of Patent: Jan. 4, 2022

(54) COMMUNICATION METHOD AND DEVICE

(71) Applicants: PRODOSE, Bessieres (FR); Morou Boukari, Toulouse (FR)

(72) Inventor: Morou Boukari, Toulouse (FR)

(73) Assignees: PRODOSE, Bessieres (FR); Morou Boukari, Toulouse (FR)

( * ) Notice: Subject to any disclaimer, the term of this patent is extended or adjusted under 35 U.S.C. 154(b) by 0 days.

(21) Appl. No.: 16/755,099

(22) PCT Filed: Oct. 9, 2018

(86) PCT No.: PCT/FR2018/052487
§ 371 (c)(1),
(2) Date: Apr. 9, 2020

(87) PCT Pub. No.: WO2019/073162
PCT Pub. Date: Apr. 18, 2019

(65) Prior Publication Data
US 2020/0242624 A1    Jul. 30, 2020

Related U.S. Application Data

(60) Provisional application No. 62/687,626, filed on Jun. 20, 2018, provisional application No. 62/646,773, (Continued)

(30) Foreign Application Priority Data

Oct. 23, 2017  (FR) ...................................... 1759992

(51) Int. Cl.
*H04N 7/18*  (2006.01)
*G06Q 30/00*  (2012.01)
(Continued)

(52) U.S. Cl.
CPC ............. *G06Q 30/016* (2013.01); *G06F 3/14* (2013.01); *G16H 80/00* (2018.01); *H04N 7/18* (2013.01)

(58) Field of Classification Search
CPC .......... H04J 14/02; G06F 3/14; G06Q 30/016; G06Q 30/0281; G16H 80/00; H04N 7/18
(Continued)

(56) References Cited

U.S. PATENT DOCUMENTS 6,289,181 B1    9/2001  Lau et al.
6,369,847 B1    4/2002  James et al.
(Continued)

FOREIGN PATENT DOCUMENTS

EP    2945341 A1    11/2015
FR    2950158 A1    3/2011
(Continued)

OTHER PUBLICATIONS

Ostman, Hanna, "The "smart fitting room" concept," RFID Arena, Jan. 3, 2013.
(Continued)

*Primary Examiner* — Gims S Philippe
(74) *Attorney, Agent, or Firm* — Nixon & Vanderhye

(57) ABSTRACT

Disclosed is a real-time communication method between two persons, one referred to as client located in a client space and the other referred to as advisor located in an advisor space, the method making available to the advisor, the images and the sound of the client requesting advice, instructions and indications regarding design, production, use, utilisation, repair, maintenance, consultation, localisation, destruction, disposal, localisation and elimination and guidance for one or more products located in or moving through a real physical space referred to as product space, and making available to the client the images and the sound
(Continued)

of the advisor interacting with the images of the client space and/or the product space. Also disclosed is a device for implementing the above method.

30 Claims, 7 Drawing Sheets

Related U.S. Application Data filed on Mar. 22, 2018, provisional application No. 62/609,366, filed on Dec. 22, 2017, provisional application No. 62/570,367, filed on Oct. 10, 2017.

(51) Int. Cl.
*G16H 80/00* (2018.01)
*G06F 3/14* (2006.01)

(58) Field of Classification Search
USPC .......................................................... 348/143
See application file for complete search history.

(56) References Cited

U.S. PATENT DOCUMENTS

| | | | |
|---|---|---|---|
| 6,434,530 | B1 | 8/2002 | Sloane et al. |
| 9,361,011 | B1* | 6/2016 | Burns ................. G06K 9/00771 |
| 9,384,402 | B1 | 7/2016 | Furman et al. |
| 10,026,108 | B2* | 7/2018 | Jackson ............. G06Q 30/0601 |
| 2002/0111890 | A1* | 8/2002 | Sloan ..................... G06Q 40/00 |
| | | | 705/36 R |
| 2002/0143633 | A1 | 10/2002 | Kunstadt |
| 2010/0205541 | A1* | 8/2010 | Rapaport .............. G06F 16/285 |
| | | | 715/753 |
| 2010/0318675 | A1* | 12/2010 | Nassor .................... H04L 47/27 |
| | | | 709/235 |
| 2012/0266258 | A1* | 10/2012 | Tuchman ........... G06Q 30/0635 |
| | | | 726/28 |
| 2013/0046637 | A1 | 2/2013 | Slutsky et al. |
| 2016/0063893 | A1 | 3/2016 | Kanuganti et al. |
| 2017/0132682 | A1 | 5/2017 | Jones et al. |
| 2017/0215071 | A1* | 7/2017 | Jayanthi ................ H04W 4/023 |

FOREIGN PATENT DOCUMENTS

| | | |
|---|---|---|
| FR | 2993681 A1 | 1/2014 |
| GB | 2329258 A | 3/1999 |
| WO | 0043912 A | 7/2000 |
| WO | 0172027 A1 | 9/2001 |
| WO | 2017079015 A1 | 5/2017 |

OTHER PUBLICATIONS

International Search Report (ISR), dated Feb. 22, 2019, from corresponding international application No. PCT/FR2018/052487.
Zhang, W., Matsumoto, T., Liu, J., Chu, M., & Begole, B. (Jan. 2008). "An intelligent fitting room using multi-camera perception." IUI 2008 : proceedings of the 13th [i.e. 12th] International Conference on Intelligent User Interfaces. Gran Canaria, Spain, Jan. 13-16, 2008, ACM, New York, NY, USA (pp. 60-69). Cited in ISR.

* cited by examiner

COMMUNICATION METHOD AND DEVICE

FIELD OF APPLICATION OF THE INVENTION

The present invention relates to the field of the communication between a person requesting an assistance and/or an expertise and a person that may provide said assistance and/or said expertise and notably to the adaptations for implementing such a communication in the best conditions.

DESCRIPTION OF PRIOR ART

Such a communication may be implemented in various situations and notably:
- during the sale of products by commercial areas receiving clients, the communication for providing the sale and the act of purchase in the best conditions,
- during remote medical consultations,
- during the distribution of products such as medicinal products,
- during the maintenance of equipment, products and infrastructure,
- during the assistance with the control of flying or rolling vehicles,
- during the establishment of military actions.

In the field of sales by commercial areas receiving clients, the purchasing process by a client in a store having a sales area with making available of products is in competition with the remote purchasing process carried out online by means of a computer tool with a virtual sales area. Thus, the stores (small or large) for selling and distributing products and service are currently facing a decrease in the visits thereof and in the appeal thereof with the development of online sales sites via Internet of products in the past sold or distributed by said stores or of new products that said stores would have been able to distribute.

Yet the client obtains a number of advantages in coming to the commercial area. For example, the client may interact with the product, handle same, try same. The client may also obtain advice from the staff present.

The reduction of visits and of appeal is partly related to the lack or to the reduction of the number of staff intended for said advice inside said stores (the clients spending a lot of time finding advisor staff or waiting the turn thereof in order to obtain advice) and/or the lack of qualification, competence and technical training of the advisory staff within said stores.

Making available said advice currently requires the presence over a wide time frame of qualified staff, which constitutes a cost for the sales areas. Furthermore, not all clients need advice and not all products need a test or advice on use.

A technical solution comprises making available to the clients located in the sales area, presentation videos of products sold projected on screens arranged, for example, on aisle end displays. Such a solution animates the shelf and constitutes an advertising process. Nevertheless, same is not intended for a client in particular and is projected towards any person passing in front of the screen whether or not same is interested in the product subject of the video.

Another technical solution comprises making available to clients located in the sales area consoles for accessing the portal or the website of the store. Such a console reproduces the same services as the online purchase site with the additional possibility of going to see, try or hold the product. For example, the site may make available videos pre-made with advice on use, installation, etc.

Thus, the store creates a content, suitable or not, made available to clients on request of said latter by activating links available on the console for this purpose.

Another technical solution comprises making available to clients located in the sales area consoles for scanning barcodes conventionally associated with each product. Such a console not only makes it possible to provide the price but also other information prepared about the product by the store or by the manufacturer. Technologies also exist in the field of clothing, which, after having scanned a photo or the body of the client, make it possible to virtually try on the products on a virtual platform where the image of the product is placed on the image of the client.

Nevertheless, it is understood that all of said various technical means do not make it possible to replace the advice from a trained professional to the client.

One of the fields wherein said replacement is to date prohibited, for example, in France, concerns the dispensing of medicinal products. Indeed, conventionally the patient must submit to the chemist a prescription dispensed by a doctor consulted beforehand. The chemist in direct contact with the patient dispenses the required medicinal products or replaces same with other equivalents and/or generics. With regards to medicinal products dispensable under prescription, same are not sold over the counter and the presence of a chemist is required. Yet, the organisation of the dispensing of medicinal products notably at night, seems to be able to be optimised.

Thus, the communication with medical experts and/or chemists for the purposes of dispensing of care and/or medicinal products are yet to be optimised.

During the maintenance of equipment, products and infrastructure, in a workshop, a factory, an operator may need to implement a communication with an expert of the operation that the operator is carrying out.

During the establishment of military actions, a soldier may require tactical advice in order to resolve the difficulties to which the soldier is faced.

For an assistance with the control of vehicles, the driving of vehicles may require a request for advice, emergency assistance.

Thus, it becomes apparent that a plurality of situations exist where a communication with an expert, an advisor is necessary. It also becomes apparent the notions of client for a person having need of advice, assistance, expertise or same of product for a product, a situation whereon may interact the advisor/expert must be understood according to a broad meaning.

Nevertheless, for the various situations cited said communication is only useful if an exchange of images is implemented. The problem is that such a real-time exchange requires complex means managing a large volume of data.

These various drawbacks are also obstacles to the development of communications between a person referred to as client and another person referred to as advisor that may provide same with the assistance, expertise required.

DESCRIPTION OF THE INVENTION

On the basis of this state of affairs, the requesters conducted research aiming to optimise the communication for the request and real-time remote supply of an expertise and of a technical assistance.

This research led to the design and to the implementation of a real-time communication method between at least one person referred to as client located in or moving through a real physical space known as client space and at least one remote person referred to as advisor located in or moving through a real physical space known as advisor space for the real-time provision by the advisor to the client of instructions and indications regarding design, production, use, utilisation, repair, maintenance, consultation, localisation, destruction, disposal, localisation and elimination, and guidance of one or more products located in or moving through a real physical space referred to as product space, which client space is provided with one or more means for receiving and displaying images, which display means are positioned at a distance clearly defined in relation to the client such as to enable same to clearly see the images displayed, which advisor space is provided with one or more means for receiving and displaying images.

This communication method is noteworthy in that it comprises the following operations:

carry out a capture of the images and of the sounds of the client in the client space thereof, and/or of the products in the product space thereof, and/or of the client and of the products in the client space and the product space, by means of image sensors and of sound sensors, which mobile and/or fixed image and sound sensors are located in or move through a real physical space referred to as image capture space, transmit thanks to digital connections (wired and/or wireless) said images and sounds captured to the advisor, display said images received on display means located in the advisor space, position the advisor next to said images displayed such as to enable same to interact with the images displayed either directly or indirectly (via pointing means of laser or stick type), recapture the images and the sounds from the advisor in interaction with the images displayed on display means located in the advisor space via sensors located in a real physical space referred to as advisor image recapture space, which recapture sensors are dimensioned and positioned at a defined distance in relation to the means for displaying images located in the advisor space such that:

on one hand, to only recapture the images displayed on the display means of the advisor space and the entire body of the advisor in interaction with the images displayed and without the advisor space or the images displayed on the display means of the advisor space and a portion of the body of the advisor in interaction with the images displayed and without the advisor space or the images displayed on the display means of the advisor space and the pointing means of the advisor in interaction with the images displayed and without the advisor space, on the other hand, such as to prevent the distortion of images related to image recaptures displayed on the screens, to directly transmit said images and sounds recaptured by the image and sound sensors located in the advisor image recapture space to the client thanks to digital connections (wired and/or wireless) and to display said images received on display means located in the client space, such that the client sees the advisor move either in the client space, or in the product space.

This method is particularly innovative in that it establishes a forward and backward motion of images making it possible for the requesting client to obtain the image of an advisor interacting with the images that the client obtains.

The communication and the transmission of advice or of the expertise are thereby significantly improved.

In addition, the superimposition of the image of the advisor interacting with another image constitutes a technical means preventing a processing of the image that is too heavy and facilitates direct transmission.

Such a method finds applications in a number of fields such as:

sales, remote medical consultations, dispensing of medicinal products, military action, vehicle driving assistance, etc.

According to another particularly advantageous feature, the method has associated or not the following features:

the client space is identical to the product space, the client space is identical to the image capture space, the client space, the image capture space and the product space are identical, the word product designates at least one of the following categories:

inert physical products, living physical products, living beings (humans or animals).

(Here, this is not to claim a living being but to expand the meaning of the word "product" so that the object of the exchange of images, of the communication can be a human being such that this may be conceived for example in a medical application for an intervention on a patient)

the client is in direct physical contact with the product or products, the client is in indirect physical contact with the product or products, the image and sound sensors located in or moving through the image capture space are mounted on land or maritime flying machines.

According to another feature of the invention, the client issues, before the operations of the method, a request for provision of instructions and indications regarding design, production, use, utilisation, repair, maintenance, consultation, localisation, destruction, disposal, localisation and elimination, and guidance of one or more products with the advisor.

According to another particularly advantageous feature of the invention, the client makes the search request thereof verbally or in writing in natural, human language on a peripheral unit referred to as client, which client peripheral unit is equipped with:

a module containing artificial intelligence enabling same to interpret and analyse the request of the client, sensors enabling same to dialogue and interact:

directly with one or more products, and/or indirectly via the client, which client being in interaction, in connection (in direct physical contact) with the product or products, at least one video sensor for filming the client in interaction in connection (contact) with the product or products, means for displaying images, videos and technical data of products, which client peripheral unit identifies the type of product, analyses, processes, interprets the request of the client and generates the sorting and selection conditions that same sends to at least one central unit referred to as server, which server central unit may contain data on the type of products and data on the peripheral units referred to as advisors with which same is in digital connection and data on the advisor or manufacturer, and which server central unit, after reception of the sorting and selection conditions, selects the type of advisor peripheral unit capable of responding to the request from the client peripheral unit and from the client such as to make it possible for the advisor peripheral unit selected to receive the images and/or videos of the client in interaction, in connection, in contact with the product or products, and which advisor peripheral unit, selected enters into direct connection with a person referred to as advisor (expert, specialist in the product and the use thereof) so as to make possible the dialogue between the client and the advisor, which advisor peripheral unit is equipped with:

a module containing artificial intelligence enabling same to interpret and analyse the advice of the advisor, which advisor may communicate verbally or in writing in natural, human language, sensors enabling same to dialogue and interact with the advisor, means for displaying images and/or videos of the client in interaction in connection with the product or products, and received from the client peripheral unit by the advisor peripheral unit, at least one video sensor for filming the advisor in the process of interacting with the images and/or videos of the actual client in interaction (in connection/in contact) with the product or products, which images and/or videos of the advisor in interaction with the images or videos of the client are sent back to the client peripheral unit and displayed on the display means equipping the peripheral unit such that the client sees the image thereof or videos superimposed with the image or the video of the advisor in the process of giving same the analysis and the technical expertise.

According to another particularly advantageous feature of the invention, the client peripheral unit communicates directly with the advisor peripheral unit without passing through the central unit referred to as server.

According to another particularly advantageous feature of the invention, the advisor peripheral unit enters into relation with other advisor peripheral units via or not one or more intermediate servers.

According to another particularly advantageous feature of the invention, the products are mutually in connection.

According to another particularly advantageous feature of the invention, the products are equipped with means for the recognition thereof or the identification thereof by the peripheral unit.

In the field of sales, the aim of the invention in particular is to

Make the clients come back into the stores, increase the visits of stores selling products and or services (Re-looking, food, clothing, household appliances, haircare or any other product);

Make it possible for the client to be able to compare the technical performances of a plurality of products directly in the store and within a very short period of time without having to wait for or search for a sales advisor in the store;

Make it possible for the client to be able to consult in the store the opinions of various clients and or users of the products;

Make it possible for the client to be able to consult in the store the trial and testing results of products by independent bodies.

Said features taken in combination or not are particularly advantageous in that same provide benefit to the client, inside the stores, of the remote advice of the best specialists of the products and services or making available thereto in the stores, of autonomous advisor tools.

According to one embodiment, the communication method of the invention is used for the sale and the distribution of products in a point of sale and/or of physical distribution to a client physically located in the point of sale and/or of physical distribution where said product is found, noteworthy in that it comprises creating a physical reception space of the client, equipping said reception space with means for capturing the sound and the image of the client inside the reception space, equipping said reception space of the client with remote means for communicating the images and the sound captured of the client, equipping said reception space of the client with means for projecting and displaying images and sound received outside of the reception space of the client, creating a physical reception space of a physical advisor remote from the reception space of the client, equipping said reception space of the advisor with means for projecting and displaying images and sound from the remote communication means of the reception space of the client, equipping said reception space of the advisor with means for capturing the sound and images of the advisor in interaction with the images and the sound of the client from the remote communication means of the reception space of the client, equipping said reception space of the advisor with direct and remote communication means to the projection and display means equipping the reception space of the client, of the images and of the sound captured of the advisor in interaction with the images and the sound of the client from the remote communication of the reception space of the client, having on display means to the client in the reception space of the client, the images and the sound captured of the advisor in interaction with the images and the sound captured of the client.

Thus, a store no longer needs to have a qualified advisor for each product that same sells while continuing to make available said advice.

Said advice may thus be given by persons located in a different store, by the manufacturers of products, by persons hired and trained for said service.

The advisor no longer needs to be located in the point of sale. Thanks to the invention, the advisor nevertheless interacts with the images of the client. Similarly, the client sees the advisor interact with the image thereof and may therefore obtain the best possible advice.

According to another feature, the client peripheral unit and the client that uses same are located in a physical store for selling products.

Thus, it is understood that the method of the invention makes it possible to define a new economical and industrial model of the sales and distribution services by relocating, rationalising and optimising the service of the advice.

Said advisor service may be particularly optimised by involving persons who may not be usually present or available. Thus, highly specialised persons, such as experts, the manufacturers of products or even the designers of products may assume said services. For example, when the products are clothes, a person trying on an item of clothing of the designer of said item of clothing may, thanks to the invention, benefit from advice from said designer.

It is then understood that the advisor service and making it available to clients may be highly valued.

Said advisor service may be dedicated to products of a certain brand or products of a certain value.

By restoring the appeal thereof to physical sales areas and by reducing the operating costs thereof, the invention provides the longevity thereof and not only contributes to the maintenance of jobs but also to the creation of more advisor jobs.

In the field of the distribution of medicinal products, the invention offers the possibility of having the presence of a chemist having a visual contact with the patient without the chemist being physically present. According to another feature of the invention, the product is a medicinal product, the client is a patient, the advisor or advisors are a doctor and/or a chemist. The distribution of medicinal products notably at night may then be significantly improved without needing the mobilisation of a large number of staff.

The area for distributing medicinal products may then consists of an automatic dispenser supplied by a stock from a chemist, from a commercial structure selling medicinal products, etc.

According to another particularly advantageous feature of the invention, the product may be a material product or a service.

According to another particularly advantageous feature of the invention, the method comprises detecting an interaction between the client and the product on sale for purposes of automatically making available in the point of sale a means of activation by the client of a remote communication with an advisor not physically located close to the client.

The advisor is then only involved when an interactivity between a product and a client is detected and when the client requires same. The advisor involved may thus be specialised in the product or the use thereof. The advisor service may be subcontracted.

According to another particularly advantageous feature of the invention, the method comprises detecting the visual interaction of the product with the client. Indeed, sensor type technical means exist associated with or not to an artificial intelligence detecting the direction of the glance of a person or the interest that same may show in one direction in particular. Once the interest for a product has been detected, the method of the invention may make available to the client a communication with an advisor.

According to another particularly advantageous feature of the invention, the method comprises detecting the material interaction, that is to say, the contact between the product and the client. The detection of such an interaction may be implemented by a plurality of means such as:
  the detection of the contact by a capacitive technology,
  the detection of the removal of the product from the display stand thereof,
  the visual detection of the taking of the product by the client,
  the detection/recognition of labels and other codes associated with the product held by the client,
  etc.

Thus, inside the same shelving, products may be distinguished from others depending on whether advice is available or not.

According to another particularly advantageous feature of the invention, each of the advisor or client spaces is fixed or mobile.

According to another particularly advantageous feature of the invention, the method is applied in at least one of the following situations of request for advice or for assistance:

request for advice for the purchase of a product by communication of the client with a specialist advisor,
  request for advice for a health condition by communication between a patient and a medical advisor,
  request for advice for a health condition by communication between a patient caregiver and a medical advisor,
  request for remote dispensing of medicinal products by communication between a patient and a chemist and/or a doctor,
  request for advice for the maintenance of a product by communication between a user of the product and a specialist of said latter,
  request for assistance in the driving of a vehicle by communication between a passenger or a driver of the vehicle with a specialist of said driving,
  request for assistance on a military operations site between a soldier and a military advisor.

Thus, according to another feature of the invention, the product is a vehicle wherein is found the client, the advisor is an expert of said vehicle and/or of the environment wherein said vehicle moves.

In the field of the distribution of medicinal products, the interaction detected is located between the patient and the prescription thereof and/or between the patient and the locked enclosure wherein are stored the medicinal products that may not be sold and therefore removed from the enclosure without the intervention of a chemist advisor who has dialogued beforehand with the patient.

A plurality of other features of the method have been invented for an application of the invention to the dispensing of medicinal products where according to another feature, the products distributed are medicinal products and the advisor is a chemist. Indeed, as explained above, the method of the invention by proposing a communication and an interaction with a remote advisor makes it possible to envisage the intervention of a chemist, intervention necessary according to certain legislations for the dispensing of medicinal products.

For such an application, the invention is noteworthy in that it comprises the plurality of features listed below to be taken, in combination or not.

The method comprises equipping said reception space with at least one of the following means:
  means for reading the social security card,
  means for reading a prescription,
  means for reading a payment card.

Said chemist reads the prescription transmitted, processes same and selects the medicinal product or products to be dispensed.

The method comprises checking the dispensing of the prescription with the health insurance fund to which the client is affiliated.

The method comprises putting said chemist in contact with a doctor.

The method comprises placing the medicinal products in a locked storage enclosure and transmitting to said chemist the images of the medicinal products in the process of being distributed before the removal thereof from the storage enclosure in order to retain same by preventing same from being dispensed in the event of error.

Furthermore, it is necessary to authorise the chemist to:
  check the identity of the client/patient,
  check the earlier date of dispensing of the medicinal products,
  replace the prescribed medicinal products with generics.

The various technical sub-assemblies equipping the client space and the various communications provided by said latter make said actions possible. Also, the fact that the chemist is in connection with the doctor treating the patient makes it possible to control the veracity of the prescription but only in the case where said doctor can be contacted.

To prevent said frauds, another automatic control introduced is the following: the dispenser is equipped with means for establishing a digital connection with the health insurance fund or the health mutuals and for consulting the electronic healthcare sheet sent automatically by the doctor to the health insurance funds and to the health mutuals after each consultation of the patient. Said electronic healthcare sheets are kept in the digital databases of the health insurance funds.

Still in the medical field, according to another particularly advantageous feature of the invention, the method comprises equipping said reception space of the client with a plurality of means requiring the presence of a third person using said means at the service of the client under the orders of said advisor. Said feature of the method makes it possible to envisage that in addition to a product such as a medicinal product, the client may seek healthcare that may only be carried out by a third person under the supervision of a doctor not physically present, by using or not the means located in the reception space. The product sought by the client/patient and then distributed with the authorisation of the medical consultant is therefore a prescription.

According to another particularly advantageous feature of the invention, the method comprises directly transmitting to the advisor, the images of the client carrying the product. Such a feature will make it possible for the advisor to have a visual contact with the client. In addition, the advisor will be able to obtain the image of the client carrying the product in order to make sure that this is in fact the product on which the advisor will give the advice and also in order to advise the client in the handling thereof.

According to another particularly advantageous feature of the invention, the method comprises directly transmitting to the client, the images of the advisor. Such a feature will make it possible for the client to establish a visual contact with the advisor who will be able to carry out a demonstration or apply the advice thereof whilst holding the same product.

For this, according to another particularly advantageous feature of the invention, the advisor is located in a store and/or a storage location with the same shelves and/or the same products as same where the client is located. Thus, the client sees what the advisor has and is not disoriented by a change in environment. Similarly, the advisor sees and therefore knows what the client has therebefore and may guide same if necessary towards other products. In addition, according to another particularly advantageous feature, the advisor is in interaction (in connection/in contact) with other products, which products are in interaction (in connection/in contact) with the advisor peripheral unit.

According to another particularly advantageous feature of the invention, the method is noteworthy in that it comprises superimposing on a single image referred to as superimposition, the images of the advisor and same of the client and of directly transmitting to the advisor and to the client said superimposed image showing the advisor in interaction with the image of the client.

Thus, the client and/or the advisor has a viewing means where same appears side-by-side with the client. This is a superimposition of image and not a juxtaposition. The visual background on which appear the two images may be constituted indifferently:

of an image of the physical location where the client is located,
of an image of the physical location where the advisor is located,
of an image of a virtual location.

According to another particularly advantageous feature of the invention, the method is noteworthy in that the image transmitted to the advisor is a virtual image of the client and/or that the image transmitted to the client is a virtual image of the advisor.

The superimposition of the image and/or the creation of a virtual image of the contact person are carried out by a software solution or by means of artificial intelligence. If the client and/or the advisor already has a virtual image, this virtual image may be used in order to be diffused on the superimposed image.

According to another particularly advantageous feature of the invention, the method is noteworthy in that it comprises an operation for marking the product benefitting from an advisor service by means of a visual sign that can be recognised by the detection means and/or by the client.

The invention also relates to the device for implementing such a method.

Such as device associates the detection means with the means for taking views, projection and display.

According to one particularly advantageous feature of the invention, the device is noteworthy in that it comprises at least one client peripheral unit made available to the client and comprising:

a module containing artificial intelligence enabling same to interpret and analyse the request of the client,
sensors enabling same to dialogue and interact:
directly with one or more products,
and/or indirectly via the client, which person being in interaction, in connection (in direct physical contact) with the product or products,
at least one video sensor for filming the client in interaction (in connection/in contact) with the product or products,
means for displaying images, videos and technical data of products,
means for displaying images and/or videos of the advisor in interaction with the images or videos of the actual client in interaction with the product or products such that the client sees the image thereof or videos superimposed with the image or the video of the advisor in the process of giving same the analysis thereof and/or the technical expertise on the product or products.
a server central unit that selects the type of advisor peripheral unit according to the sorting and selection orders received from the client peripheral unit,
at least one other peripheral unit referred to as advisor made available to an advisor including:
a module containing artificial intelligence making it possible for same to interpret and analyse the advice of the advisor, which advisor communicates verbally or in writing in natural, human language,
sensors enabling same to dialogue and interact with the advisor,
means for displaying images and/or videos of the client in interaction with the product or products and received from the client peripheral unit by the advisor peripheral unit,
at least one video sensor for filming the advisor in the process of interacting with the images and/or videos of the actual client in interaction with the product or products, which images and/or video of the advisor in interaction with the images or videos of the client are sent back to the client peripheral unit and displayed on the display means equipping the client peripheral unit such that the client sees the image thereof or videos superimposed with the image or the video of the advisor in the process of giving same the analysis and the technical expertise. The client and/or the advisor who may be a supplier or a manufacturer, communicates the questions thereof in natural, human, normal language that are analysed by the interpretation and analysis module equipping the advisor and client peripheral units.

To implement the various functions, the peripheral units advantageously comprise video sensors. Said video sensors such as cameras may be used to diffuse the image directly to the client and/or to the advisor or to acquire the movements, facial expressions and other physical parameters for the purposes of diffusion to the client and/or to the advisor of a representative and animated virtual image of the contact person thereof.

According to another particularly advantageous feature of the invention, the client peripheral unit is a means for distributing products supplied as products by a locked product storage area and not accessible for the client, the distribution of products requiring beforehand the dialogue between client and advisor and the authorisation of the advisor. It is understood that such a device is suitable for the dispensing of products such as medicinal products to clients/patients who will consult a chemist not physically present beforehand. It is then normal that the medicinal products are located in a locked storage area not accessible for the client which only has access to the medicinal products effectively dispensed and therefore extracted from said storage area.

The implementation of the real-time transmission of images such as described in the above method steps encounters a plurality of difficulties described below:

When the camera films the advisor in the process of interacting with the images of the client displayed on the display screen of the advisor peripheral unit, a time-lag is created between the image plane of the advisor and the plane of images of the client displayed, When the camera films the advisor in the process of interacting with the images of the client displayed on the display screen of the peripheral unit, a disproportion becomes apparent between the image of the advisor and the image of the client; the image of the advisor may seem much larger in relation to same of the client. To increase the size of the image of the client displayed on the display means of the peripheral unit of the advisor, it is possible to zoom in on the camera but the increase of the size for displaying the client on the display screen of the advisor peripheral unit makes it necessary to have a very large display screen with very high purchase prices, the software processing of the images for processing said time-lags requires a very large and very expensive installation, the possibility of making the advisor move on green screen requires a very large and very expensive installation and is detrimental to a true interactivity of the advisor with the images of the client.

To solve said technical problems, the device of the invention is noteworthy in that the cameras of the advisor peripheral unit are equipped with specific means.

According to a first feature, in order to raise the image plane of the client to the level of the image plane of the advisor and solve the problem of disproportion of the sizes of the client and of the advisor, the camera is equipped with a correction means comprising a bifocal focus lens, which lens consists of two half-lenses (symmetrical or not) of different dioptries or of different magnifications and the gluing (assembly) axis of which is located in a plane perpendicular to the axis of the lens of the camera.

This bifocal focus lens is mounted or glued on the face of the lens of the cameras of the advisor space. When an observer faces the lens of the camera, the dioptry of the lens or the magnification of the lens may vary increasingly from left to right and vice versa. The lens may be provided with a means for rotating same about same at 360° or for moving from left to right so as to make move from left to right or from right to left the assembly axis of the two half-lenses. The correction means consists of a half-lens of a dioptry or of a magnification other than the air, the other half being the free air.

According to another feature, the correction means consists of a progressive lens of a dioptry or of a magnification varying from left to right increasingly or decreasingly for an observer facing the lens of the advisor camera.

The fundamental concepts of the invention being above disclosed in the most elementary form thereof, other details and features will become more clearly apparent upon reading the following description and with regard to the appended drawings, giving by way of non-limiting examples, embodiments of methods and devices according to the invention.

DETAILED DESCRIPTION OF PREFERRED EMBODIMENTS

Figure 1:
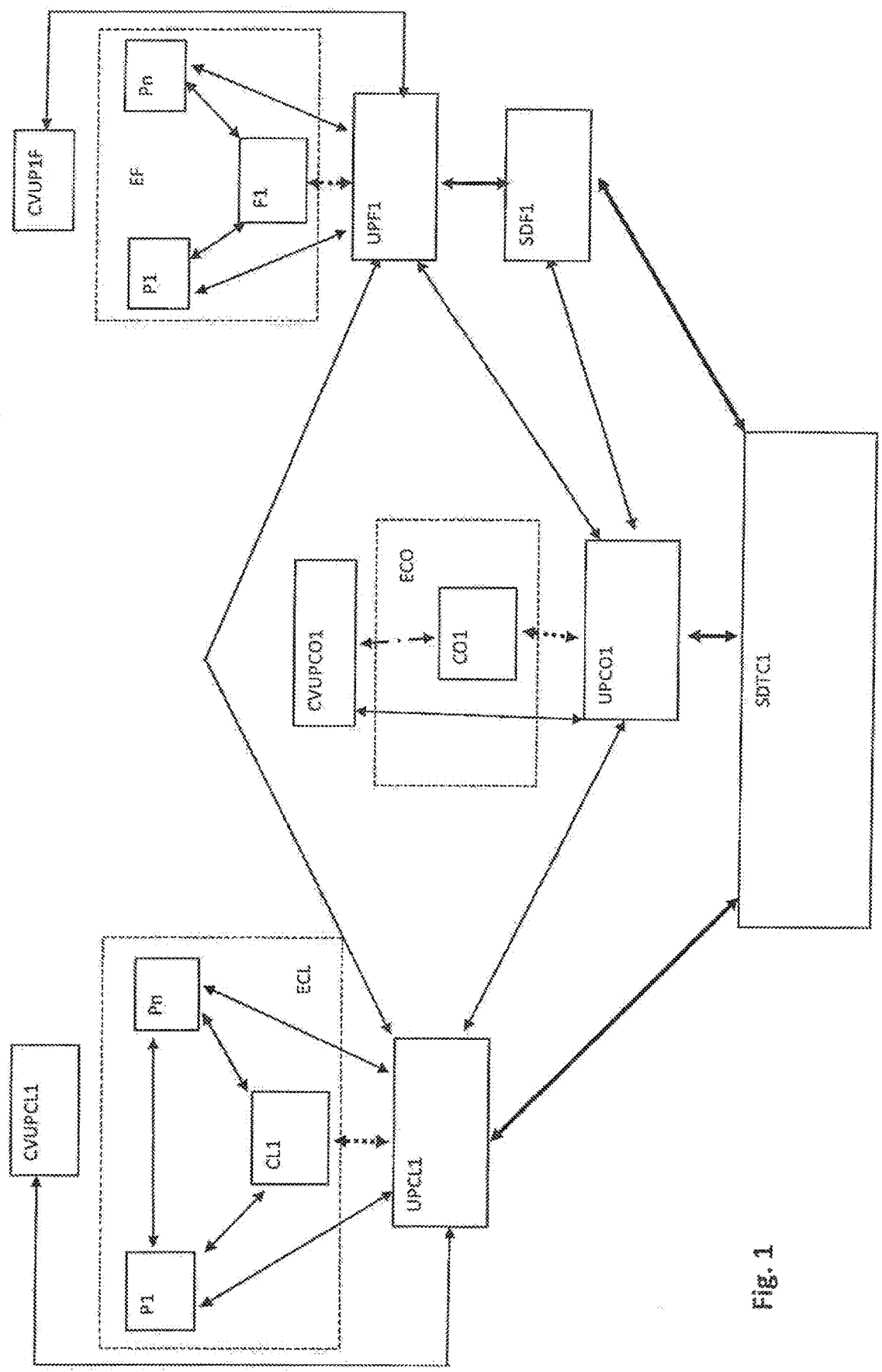
FIG. 1 is a schematic drawing of a flow chart illustrating one embodiment of a device according to the invention.
Figure 2:
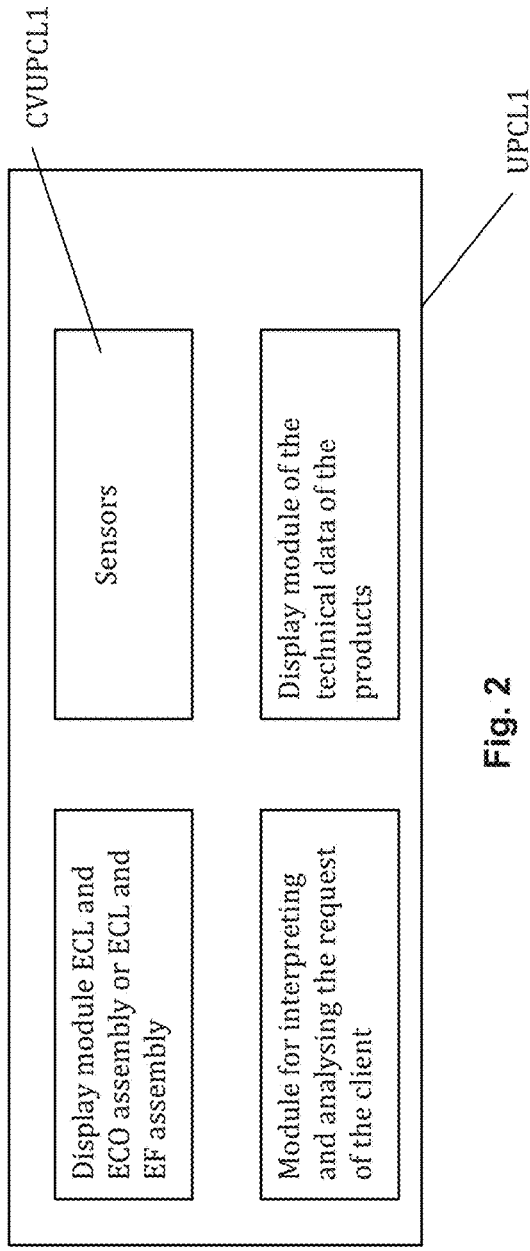
FIG. 2 is a schematic drawing illustrating the functional modules of one embodiment of a peripheral unit or console made available to the client.

As illustrated on the drawing in FIG. 1, the client CL1 is in direct (by physical touching) or indirect (capturing of the glance on the product) interaction with one or more products P1 to Pn. The client CL1 also interacts with the peripheral unit or console UPCL1. Indeed, as illustrated on the drawing in FIG. 2, said peripheral unit UPCL1 comprises means (sensors, sound sensors, touch screen, screen with keypad, artificial intelligence, product code reader) making it possible for same to dialogue with the client CL1. Said dialogue may be carried out verbally or in writing. The client CL1 may communicate in natural, human, normal language. Without communication from the client CL1, the actual peripheral unit may make available to the client CL1 a service for advice or an information signal that an advisor service is available.

The peripheral unit UPCL1 also comprises:
a module for displaying the technical data of products,
a module for displaying the client and advisor or manufacturer/supplier assemblies,
a module for interpreting and analysing the request of the client.

The products P1 to Pn may be in direct or indirect interaction with UPCL1. For this, the products may be equipped with codes/elements of recognition for the identification thereof by identification means equipping the peripheral unit UPCL1 or by the client.

The client CL1 issues or not the request thereof (verbal or written or product code reading, etc.) on the peripheral unit UPCL1. The peripheral unit UPCL1 processes the interaction data and the request of the client and generates the conditions for sorting, selecting and processing the data and sends same to the central unit of the server SDTC1. The server SDTC1 selects the type of product and the advisor peripheral unit UPCO1 or corresponding manufacturer or supplier peripheral unit UPF1.

Figure 3:
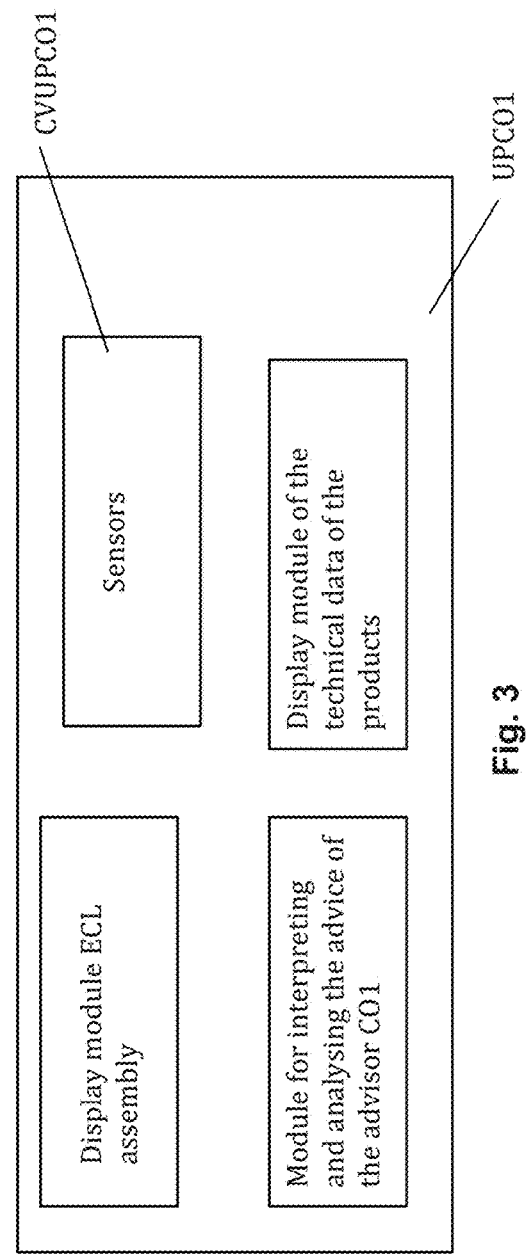
FIG. 3 is a schematic drawing illustrating the functional modules of one embodiment of a peripheral unit or console that the advisor has.

The advisor peripheral unit UPCO1 is in relation with at least one advisor CO1. As illustrated on the drawing in FIG. 3, said advisor peripheral unit UPCO1 comprises:
a module for displaying the client assembly ECL,
a plurality of sensors,
a module for interpreting and analysing the advice of the advisor CO1,
a module for displaying the technical data of products.

The manufacturer or supplier peripheral unit UPF1 is in relation with at least one technical person F1 of the manufacturer or supplier.

Figure 4:
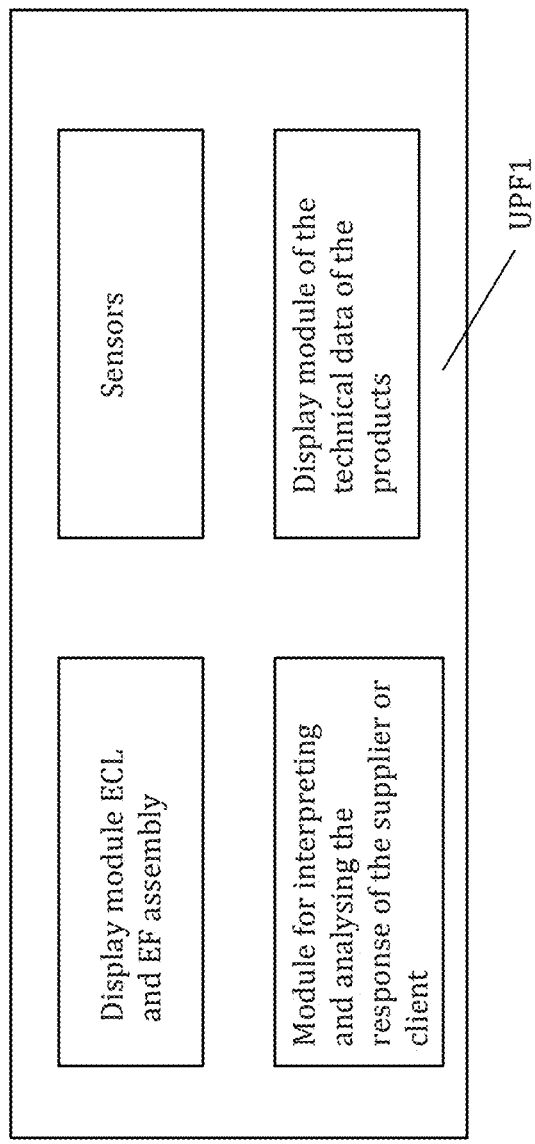
FIG. 4 is a schematic drawing illustrating the functional modules of one embodiment of a peripheral unit that the manufacturer or the supplier of the product has.

As illustrated on the drawing in FIG. 4, the peripheral unit of the manufacturer or of the supplier UPF1 comprises as UPCO1:
a module for displaying the client assembly ECL and the manufacturer/supplier assembly,
a plurality of sensors,
a module for interpreting and analysing the response of the supplier F1 or of the client CL1,
a module for displaying the technical data of products.

A communication is then created between the client CL1 and the advisor CO1 or the technical or commercial person of the manufacturer or supplier F1.

Of course, the server SDTC1 may send back technical data of the products and/or comparisons of various products and/or opinions of clients and/or the results of trials and tests directly to the client CL and on the peripheral unit UPCL1 and this, without having to query UPCO1 or UPF1.

The server unit SDTC1 contains technical and commercial data from the actual stores, manufacturers and/or suppliers of products, consultancy companies, clients and trial and testing bodies. Said data is constantly updated.

Of course, a plurality of peripheral units may exist, a plurality of units referred to as servers that are mutually in relation by digital connection.

These units referred to as servers may be in relation with servers or websites in order to collect other technical and commercial data, opinions of clients, results of tests and trials of products.

The peripheral units UPCL1, UPCO1, UPF1 may also be mutually in direct connection by digital connection.

The peripheral unit UPCO1 comprises means (sensors, sound sensors, touch screen, screen with keypad, artificial intelligence, product code reader) making it possible for same to dialogue with the advisor CO1. Said dialogue may be carried out verbally or in writing. The advisor CO1 like the client CL1 may communicate in natural, human, normal language.

The peripheral unit UPF1 comprises means (sensors, sound sensors, touch screen, screen with keypad, artificial intelligence, product code reader) making it possible for same to dialogue with the technical person F1. Said dialogue may be carried out verbally or in writing. The staff F1 may communicate in natural, human, normal language.

Figure 8:
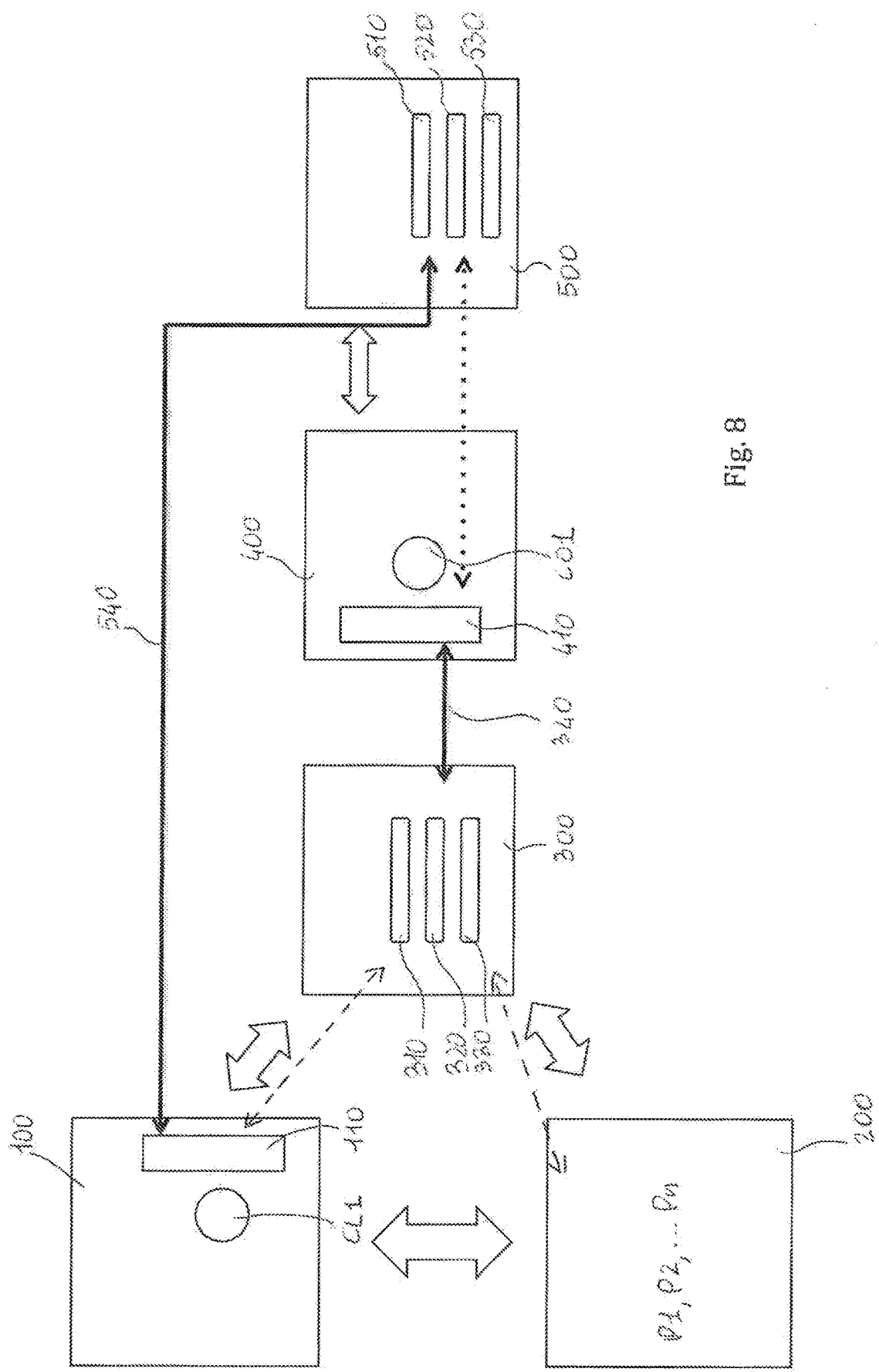
FIG. 8 is a schematic drawing of one embodiment of a method implemented in accordance with the invention.

A more global but also more precise operation is illustrated by the drawing in FIG. 8.

According to said FIG. 8, the client space 100 receives the client CL1 as well as means for displaying images and sounds 110.

The product space 200 receives the products P1, P2, . . . Pn. Said two spaces may of course communicate.

Associated with said two spaces 100 and 200, an image and sound capture space 300 equipped with sensors 310, 320, 330, etc., provides the taking of images and of sounds in the client spaces 100 and product spaces 200. From said sensors is found the CVUPCL1 video camera appearing in FIG. 1. Said image and sound capture space 300 may be confused with the client spaces 100 and/or product spaces 200. Said sensors communicate by a digital connection 340 the images and the sound captured to an advisor space 400 that receives the advisor CO1. Said advisor space 400 is equipped with means for displaying images and sounds 410. Said advisor space 400 is associated with a space 500 that recaptures the images and the sound in the advisor space 400 by means of sensors 510, 520, 530 in order to film the advisor CO1 in interaction with the videos diffused by the means 410. Said recapture space 500 may be confused with the advisor space 400. The sensors 510, 520, 530, etc., of the recapture space 500 communicate by means of the connection 540 the images and the sounds captured in the advisor space 400 to the display means 110 of the client space 100. From said sensors is found the CVUPC01 video camera appearing in FIG. 1. In accordance with the invention, the client CL1 then sees an advisor CO1 interact with the image thereof and/or with same of the product.

The communication and the connection between the sub-assemblies may vary according to the applications. Thus, for example, the connections may all pass through the Internet network and/or a wired or wireless local Intranet network. In addition, master/slave architectures may be established.

Moreover, some sub-assemblies may be mobile in order to follow the advisor CO1 or the client CL1 or the product P1 to Pn that interests same.

For example, a portable case carried by the advisor CO1 may gather together the means for receiving and displaying images and sounds of the client and/or of the product and sensors for recapturing images of the advisor CO1 interacting with the images displayed on the display means of the case.

Furthermore, what is designated as the product P1 to Pn may also vary as becomes apparent upon reading the examples described below. The example below is based on an application of the invention to a store selling clothes.

The client CL1 chooses the clothes P1 to Pn that same wants.

The client CL1 wears the clothes chosen.

The client CL1 stands in front of the peripheral unit UPCL1, which recognises the product or products worn by the client CL1. The peripheral unit UPCL1 films the client CL1 wearing the clothes (thanks at least to the camera CVUPCL1) and queries the server unit SDTC1, which in return searches for and selects the corresponding clothing consultancy company (relooking, best stylist, for example) and will put in relation the client peripheral unit UPCL1 with the advisor peripheral unit UPCO1. The actual advisor peripheral unit UPCO1 enters into relation with the advisor CO1 in order to make possible the dialogue between the client CL1 and the advisor CO1. The images and/or the videos of the client CL1 wearing the product or products are displayed on the advisor peripheral unit UPCO1. The advisor CO1 interacts with the images or videos of the client CL1 wearing the clothes and displayed on UPCO1, enters into dialogue with the client CL1 and gives same advice and shows same, for example, the places (parts of the clothes) that fit well or not the client CL1, make same try on other clothes, indicates thereto colours to choose.

The camera CVUPCO1 films the advisor in interaction with the image or the video displayed on the peripheral unit UPCO1. Said camera therefore captures the images and the sound of the advisor in interaction with the images of the client with the product.

On the peripheral unit UPCL1, the client CL1 then sees the own image thereof or video wearing the clothes and superimposed with the images of the advisor CO1 in the process of giving same the advice. The peripheral unit UPCL1, the camera CVUPCL1 and the client assembly ECL may be located inside the actual changing room located in the store.

A video screen is then located in the room referred to as client room that comprises means for displaying the images of the client superimposed with the images of the advisor, which advisor is in interaction with the images of the client.

Said means further make it possible to display the various profiles of the client on the screen without the client having to turn back and forth. Said means make it possible for the advisor to select and display on the screen of the room referred to as advisor, the images corresponding to a given profile of the client filmed by the cameras located in the room referred to as client, which profiles being front, back, right, left, head and feet profiles. Said means make it possible for the advisor to interact with a specific area of the body of the client in order to dispense thereof suitable advice. The selection of said profiles may be carried out manually by the advisor or automatically. In said latter case, said means may be equipped with artificial intelligence for interpreting the speech of the advisor, for recognising in said speech the type of profiles of images of the client to display.

The room referred to as client may also comprise means for capturing photographs, recording images of the advisor in interaction with the images of the client and optionally means for printing and/or sending said captured images on other media.

Of course, the various profiles of images of the client may be displayed on the screen located in the client room, recorded or sent without the images of the advisor.

The images displayed on the client screen or on the advisor screen may be three-dimensional images and the cameras that film may also be cameras filming according to three dimensions.

The room referred to as client constituting the reception space of the client may be located in a sales store, at the home of the client, in an aircraft, on a boat, in a vehicle on another planet. The room referred to as advisor constituting the reception space of the advisor may be located in a sales store, at the home of the advisor, in an aircraft, on a boat, in a vehicle on another planet. The example below is based on an application of the invention to a store selling products other than clothes and the client only wants to consult some technical data.

The client CL1 chooses the product or products P1 to Pn that same wants.

The client will scan using a mobile scanner or on the client peripheral unit UPCL1, the code or codes of the product or products and will issue on the peripheral unit UPCL1 a request. Said request may concern the technical features of the product or products, the operation of the product or products, the opinions of the user or users of the product or products, the results of the tests or trials of the product or products, the comparison of the various products. The peripheral unit UPCL1 will recognise the product or products chosen by the client, will analyse and interpret the request of the client and will query the server unit SDTC1 that in return will search for and select the data on the technical features of the product or products, the operation of the product or products, the opinions of the user or users of the product or products, the results of the tests and trials of the product or products, the comparison of the various products. The unit referred to as server SDTC1 will send back the results of the request on the client peripheral unit UPCL1 that will communicate same to the client CL1 in sound form and/or on screen display form.

Figure 5:
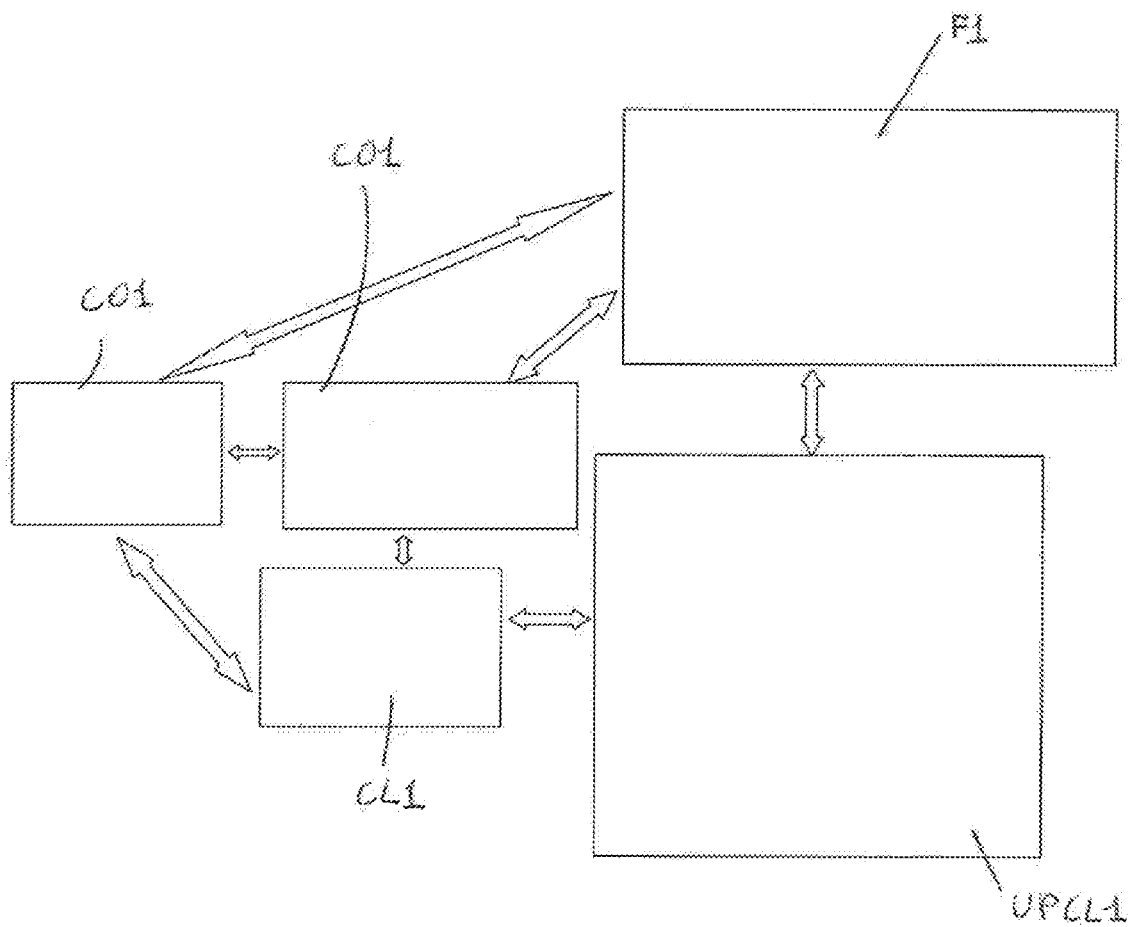
FIG. 5 is a schematic drawing of a flow chart illustrating the interactions for the implementation of a distribution of medicinal products.

An example of distribution of medicinal products according to the method of the invention is illustrated by the diagram in FIG. 5 that illustrates the various interactions.

The various elements constituting the device for implementing the method are distributed in the following manner:
Product P1=medicinal products;
Client CL1=sick person;
CL1 provided with means of the identification thereof (healthcare card, prescription, mutual card, bank card);
Advisor CO1=doctor of the sick person or CO1' remote medical consultant;
F1=remote chemist;
UPCL1 located in the medicinal product dispenser;
UPCO1 located with the medical consultant CO1;
UPF1 located with the chemist F1.

The steps of the method are the following:
The patient CL1 is equipped with one or more of the following elements:
medical prescription,
social security card,
mutual card,
payment bank card,
coin or banknote Thus, same is identified with the social security card thereof or the mutual card thereof or other means;

The patient CL1 inserts the medical prescription thereof into the scanner provided for this purpose;

An audio-video contact is established between the patient CL1 and the chemist F1;

The chemist F1 who is located remotely is equipped with one or more of the following elements:
means for receiving medical prescriptions,
means for sending new prescriptions or modified prescriptions,
means for remotely selecting the medicinal products to be dispensed,
means for receiving the optical control results of the medicinal products for verification of the medicinal products before dispensing,
means for controlling the remote dispensing of medicinal products, means for controlling the remote dispensing of medicinal products, audio-video dialogue means.

Thus, the chemist F1 receives the scanned prescription of the patient CL1 with identification of the contact details of the prescribing doctor CO1 for any contacts;

The chemist F1 analyses and inspects the prescription in order to detect any prescription errors;

If an error is detected and the error is negligible the chemist F1 corrects the error;

If an error is detected and the error needs to be corrected by a doctor, the chemist F1 enters into audio-video contact and dialogue with the prescribing doctor (doctor of the patient CO1) or failing this with another medical consultant CO1'. The dialogue may also be three-party and may involve the patient CL1 with a possibility of the audio-video dialogue with the prescribing doctor CO1 or failing this a medical consultant CO1' with the patient CL1; The doctors are equipped with means for audio-video dialogue and means for sending and receiving medical prescriptions.

The prescribing doctor CO1 or failing this the medical consultant CO1' corrects the prescription or gives the agreement thereof to the chemist so that said latter corrects the prescription. A new prescription may be issued by the prescribing doctor or failing this by the medical consultant;

Once the medical prescription has been analysed or any corrections completed, the chemist F1 issues an order for selecting the medicinal products to be dispensed, which order is remotely transmitted to the automatic dispenser that carries out the physical selection of the medicinal products;

The chemist F1 remotely controls the nature of the medicinal products to be dispensed thanks to optical control means equipping the automatic dispenser UPCL1;

The automatic medicinal products dispenser UPCL1 is equipped with one or more of the following elements:

prescription scanner,
social security card scanner or reader,
insurance card scanner or reader,
bank card payment terminal,
bank note or coin payment terminal,
audio-video dialogue means,
means for storing medicinal products,
means for sorting and selecting medicinal products,
means for printing new medical prescriptions or modified medical prescriptions,
means for optically controlling medicinal products before dispensing,
means for dispensing medicinal products to the patient,
means for affixing the mark for dispensing the medicinal products (mark that may contain the name of the dispenser, the date and the time of dispensing, etc.)

If there is payment of medicinal products, the payment order is indicated to the patient CL1;

The medicinal products remotely controlled by the chemist F1 are finally dispensed to the patient CL1;

The medicinal product dispensing mark is affixed on the prescription;

The prescription is returned to the patient CL1. If there was a prescription modification, a printout is produced of the new modified prescription.

Figure 6:
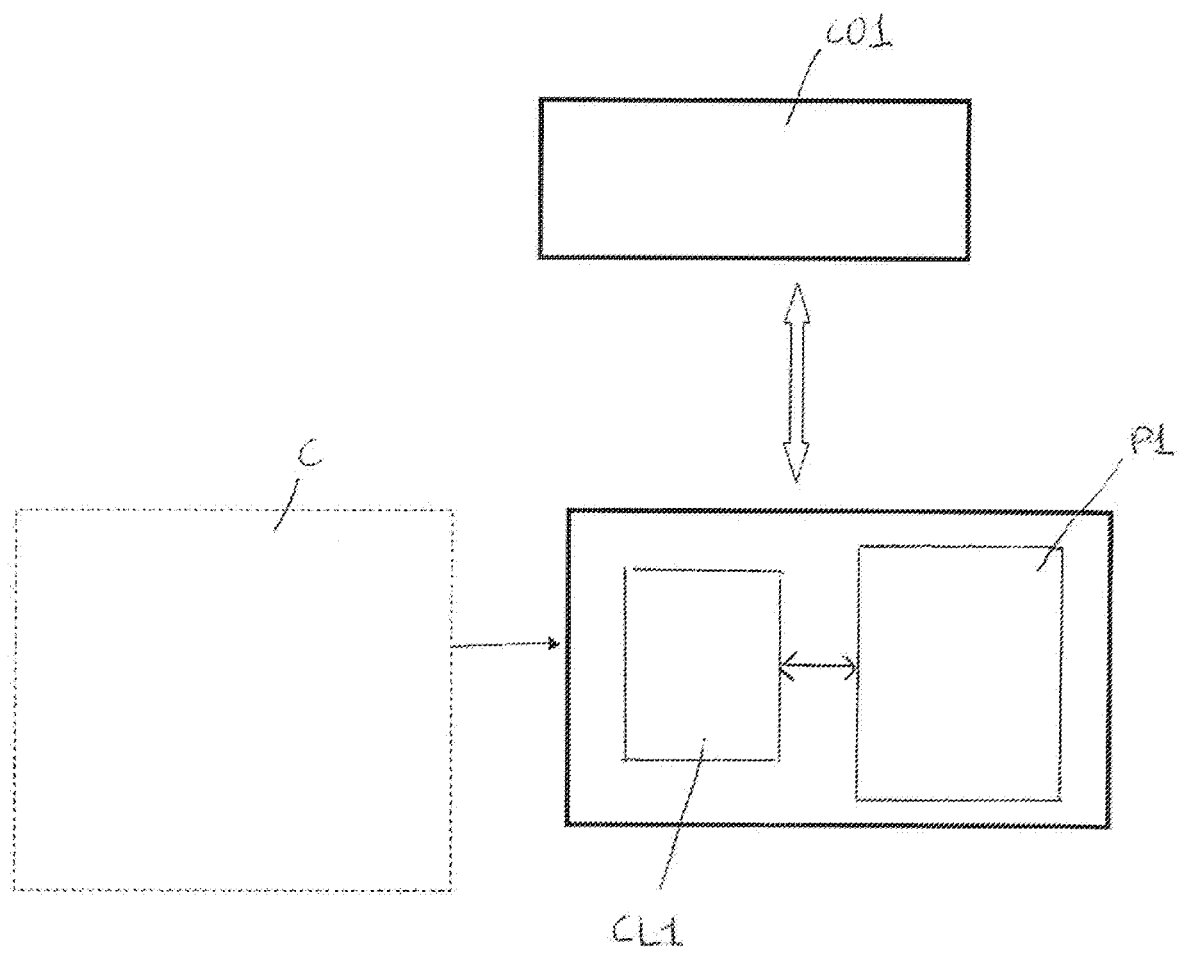
FIG. 6 is a schematic drawing of a flow chart illustrating the interactions for the implementation of a medical consultation.

An example of implementation of a medical consultation/remote medical consultancy service according to the method of the invention is illustrated by the diagram in FIG. 6 that illustrates the various interactions.

According to a first configuration (same illustrated), the consultation is carried out in the physical presence of a doctor or nurse in the same location as the patient. The product is then a patient, the client is a doctor or a nurse/requestor of advice and the advisor is an expert doctor. The various elements constituting the device for implementing the method are distributed in the following manner:

Product P1=patient or sick person;

Client CL1=doctor or nurse located in the same location as the sick person;

Said client CL1 is provided with means (sensors) for examining the sick person P1 (thus as explained above the word product may also designate a person);

Advisor CO1=doctor or expert doctor or remote specialist doctor; CL1, P1 and UPCL1 are located with the sick person P1 or with the doctor or nurse CL1 or in a medical room C or a medical centre (clinic, hospital, health centre, etc.).

The patients and doctors are equipped with the same elements as same described in the previous example.

Said medical room is equipped with one or more of the following elements:

prescription scanner,
means for printing medical prescriptions,
social security card scanner or reader,
insurance card scanner or reader,
bank card payment terminal,
bank note or coin payment terminal,
audio-video dialogue means,
means and sensors for the examination of the patient:
thermometer,
blood pressure monitor,
stethoscope,
endoscope,
any other means for examining the patient.

The method then makes it possible, for example, for nurses to consult the patients with a remote assistance from an authorised doctor thanks to a three-party audio-video dialogue between the patient, nurse and the doctor; the nurse receiving remote orders from the doctor. Said orders concern the type of measurements (or examination) to be carried out on the patient, the actions to be taken. Once all of the examinations have been performed directly with the doctor, said latter establishes a medical diagnosis and sends a medical prescription with the list of medicinal products to be taken by the patient and/or a recommendation of additional analyses to be carried out. The medical prescription and/or the document for the additional analysis (then constituting the product distributed) received in the medical room for consultation by the nurse thanks to the digital connections between the remote medical room and the consultation office wherein the nurse is located. The prescription and/or the additional analysis document is printed out by the nurse and given to the patient.

The nurse is in direct interaction with the patient.

According to a second configuration not illustrated, the consultation is carried out in the physical absence of a doctor or nurse in the same location as the sick person. The product consists of measurement means (body temperatures, blood pressure, heart beats, etc.), the client is a patient and the advisor is an expert doctor. The various elements constituting the device for implementing the method are distributed in the following manner:

Client CL1=sick person;

Product P1=measurement means (body temperatures, blood pressure, heart beats, etc.);

Advisor CO1=doctor or expert doctor or remote specialist doctor; UPCL1 located with the sick person.

The sick person CL1 is then directly put in contact with the doctor CO1 located remotely.

The example below is based on an application of the invention to the industrial maintenance. The product is then an item of equipment, a product, an infrastructure, the client is a repair maintenance operator and the advisor is an expert in said equipment, product, infrastructure. It is not specifically illustrated but repeats the principles illustrated by the drawing in FIG. 1. The various elements constituting the device for implementing the method are distributed in the following manner:

Product P1 to Pn=equipment, products (buildings, boats, aerial vehicles, land vehicles, any rolling or flying machines, etc.), infrastructure;

Client CL1=maintenance operator, repair operator;
CL1 provided with means for repairing products P1 to Pn;
Advisor CO1=expert, remote specialist;
F1=remote manufacturer of P1 to Pn;
May have a plurality of cameras CVUPCL1;
Cameras CVUPCL1 that may be selected or may be controlled remotely by CO1 or F1;
Mobile or fixed UPCL1;
Mobile or fixed camera CVUPCL1 and audio sensor;
Camera CVUPCL1 and audio sensor that may be carried by client CL1 or mounted on drone or mounted on mobile robot;
Camera CVUPCL1 that may film the products P1 to PN+the entire body of CL1;
Camera CVUPCL1 that may film the products P1 to PN+a portion of CL1 (the arms and hands, for example);
Camera that may film the products P1 to Pn but without filming the client CL1;
Display screen equipping mobile or fixed UPCL1, mounted on UPCL1 or separate from UPCL1 but digitally connected,
Display screen equipping UPCL1 that may be carried by the client CL1,
Display screen equipping UPCL1 that may be integrated into the glasses worn by the client CL1, The example below is based on an application of the invention to the assistance with the driving of vehicles. It is not specifically illustrated but repeats the principles illustrated by the drawing in FIG. 1. The various elements constituting the device for implementing the method are distributed in the following manner:

Product P1=product inside of which is located the client CL1, i.e. here a vehicle (boats, aerial vehicles, land vehicles, any rolling or flying machine, etc.),
Client space=Environment wherein moves the client CL1 and/or the product P1,
(P3+P4+P5+ . . . +Pn=other products equivalent to P1+mobile or fixed obstacles located in the environment P2)
Client CL1=pilot, driver or passenger of P1,
CL1 installed inside the product P1,
Advisor CO1=expert, remote specialist knowing the product P1, P2, P3 . . . Pn well,
F1=manufacturer of P1 to Pn, remote expert,
A plurality of cameras CVUPCL1 may be installed inside and outside of the products P1 to Pn,
Cameras CVUPCL1 that may be controlled remotely by CO1 or F1;
UPCL1 installed inside P1 and may form an integral part of the product P1,
A portion of the Camera CVUPCL1 and audio sensor being mobile or fixed,
A portion of the Camera CVUPCL1 and audio sensor being carried by the client CL1, Camera CVUPCL1 that may film the environment P2 wherein move the products P1 and P3 to Pn+the entire body of CL1+a portion or all of the product P1,
Camera CVUPCL1 that may film the environment P2 wherein move the products P1 and P3 to Pn+a portion of CL1 (the arms and hands, for example)+a portion or all of the product P1 to Pn
Camera that may film the products a portion or all of the P1 to Pn but without filming the client CL1,
Display screen equipping mobile or fixed UPCL1, mounted on UPCL1 or separate from UPCL1 but digitally connected,
Display screen equipping UPCL1 that may be carried by the client CL1,
Display screen equipping UPCL1 that may be integrated into the glasses worn by the client CL1,
During such an application, the advisor may take the control of the vehicle under the supervision or not of the client.

The example below is based on an application of the invention to military combats. It is not specifically illustrated but repeats the principles illustrated by the drawing in FIG. 1.

Figure 7:
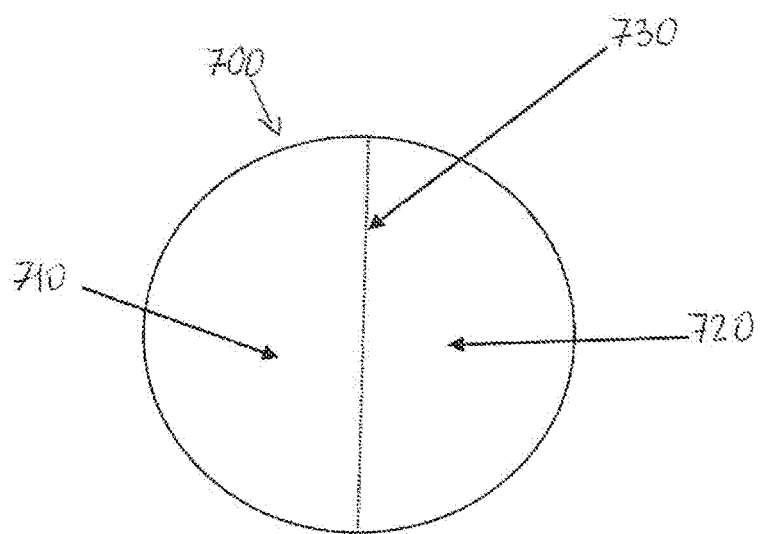
FIG. 7 is a schematic drawing of one embodiment of a bifocal lens according to the invention.

The various elements constituting the device for implementing the method are distributed in the following manner:

Product P1=product inside of which is located the client CL1=flying or rolling vehicles=boats, aerial vehicles, land vehicles, any rolling or flying machine, etc.);
P2=Environment wherein moves the client and/or the product P1 P3+P4+P5+ . . . +Pn=other products equivalent to P1+mobile or fixed obstacles located in the environment P2;
Client CL1=military;
Client CL1 may not be inside P1;
CL1 installed inside product P1 or client moving in the environment P2;
Advisor CO1=expert, remote specialist knowing the product P1 and P3 . . . Pn well;
F1=manufacturer of P1 to Pn, remote expert;
P3+P4+P5+ . . . +Pn=may be products or enemy targets located in the environment P2 and to be destroyed by the client CL1;
A plurality of cameras CVUPCL1 may be installed inside and outside of the products P1;
Cameras CVUPCL1 that may be controlled remotely by CO1 or F1;
UPCL1 installed inside P1 and forms part of the product P1;
UPCL1 may be mobile or fixed;
UPCL1 may be carried by the client CL1;
Camera CVUPCL1 that may be a 360° camera mounted on the helmet of CL1;
A portion of the mobile or fixed camera CVUPCL1 and audio sensor;
A portion of the camera CVUPCL1 and audio sensor carried by client CL1
Camera CVUPCL1 that may film the environment P2 wherein move the products P1 and P3 to Pn+the entire body of CL1)+a portion or all of the product P1;
Camera CVUPCL1 that may film the environment wherein move the products P1 to PN+a portion of CL1 (the arms and hands, for example)+a portion or all of the product P1 to Pn;
Camera that may film the products a portion or all of the P1 to Pn but without filming the client CL1;

Display screen equipping mobile or fixed UPCL1, mounted on UPCL1 or separate from UPCL1 but digitally connected, Display screen equipping UPCL1 that may be carried by the client CL1, Display screen equipping UPCL1 that may be integrated into the glasses worn by the CL1;

As explained above, the real-time exchange of images as well as the difficulty in displaying the image of the advisor interacting with the images of the client have led the applicants to propose an optical solution illustrated by the drawing in FIG. 7.

Indeed, the cameras CVUPCO1 and CVUPF1 are equipped on the lens thereof with specific means for solving the problems described above. Thus, in order to raise the image plane of CL1 to the level of the image plane of CO1 or F1 and solve the problem of disproportion of the sizes of the client CL1 and of the advisor CO1 or manufacturer F1, the camera CVUPCO1 or CVUPF1 is equipped with a correction means comprising a bifocal focus lens 700, which lens consists of two half-lenses 710 and 720 (symmetrical or not) of different dioptries or of different magnifications and the gluing (assembly) axis 730 of which is located in a plane perpendicular to the axis of the lens of the camera CVUPCO1 or CVUPF1 and which bifocal focus lens is mounted or glued on the face of the lens of the cameras CVUPCO1 or CVUPF1. When an observer faces the lens of the camera, the dioptry of the lens or the magnification of the lens may vary increasingly from left to right and vice versa. The lens may be provided with means for rotating same about same at 360° or for moving from left to right so as to make move from left to right or from right to left the assembly axis of the two half-lenses.

It is understood that the method and the device, which have been described and shown above, have been so in view of a disclosure rather than of a limitation. Of course, various adjustments, modifications and improvements may be made to the above example, without departing from the scope of the invention.

For better understanding of the drawings, a list of references with the legend thereof is provided below:

CVUPCL1: video sensor equipping the client peripheral unit and for filming the client CL1 in interaction with the products P1 to Pn, P1: Product 1,
Pn: Product n,
CL1: client 1,
UPCL1: peripheral unit connected to the client 1,
SDTC1: Technical and commercial data server no. 1,
UPCO1: advisor peripheral unit no. 1 and connected to the advisor CO1,
CO1: advisor no. 1,
CVUPCO1: video sensor equipping the advisor peripheral unit no. 1 for filming the advisor CO1 in interaction with the actual client CL1 in interaction with the products P1 to Pn,
CVUPF1: sensor equipping the supplier peripheral unit 1 for filming the person of the manufacturer or supplier in interaction with the products P1 to Pn and said actual person in interaction with the actual client CL1 who is in interaction with the products P1 to Pn,
F1: supplier or manufacturer no. 1,
UPF1: manufacturer or supplier peripheral unit no. 1,
SDF1: manufacturer or supplier data server no. 1,
ECL: client assembly consisting of the client CL1 and the products P1 to Pn,
ECO: advisor assembly consisting of the advisor 1 and the products P1 to Pn,
EF: supplier or manufacturer assembly consisting of the supplier or manufacturer no. 1 and the products P1 to Pn.

The invention claimed is:

1. A real-time communication method between at least one person, referred to as client, located in a real physical space known as a client space and at least one remote person, referred to as advisor, located in a real physical space known as an advisor space for the advisor to provide real-time instructions and indications to the client, the instructions and indications regarding design, production, use, repair, maintenance, consultation, localization, destruction, disposal, localization and elimination, guidance of one or more products located in a real physical space referred to as a product space, wherein the client space is provided with one or more receiving means and display means for receiving and displaying images, wherein the display means in the client space are positioned such as to enable the client to clearly see the images displayed on the display means located in the client space, wherein the advisor space is provided with one or more of the receiving means and the display means for receiving and displaying images, wherein image sensors and sound sensors are located in a real physical space referred to as an image capture space, wherein a real physical space referred to as advisor image recapture space is associated with the advisor space, the advisor image recapture space being provided with sensors that film the advisor in interaction with displayed images on the display means located in the advisor space to thereby provide recapture images of the advisor in interaction with displayed images on the display means located in the advisor space, the advisor space being connected to the client space via a first communication connection to communicate to the client space the provided recapture images of the advisor and thereby have the advisor provide the real-time instructions and indications to the client, the first communication connection comprising a first wired digital connection and/or a first wireless digital connection, the advisor space being connected to the capture space via a second communication connection, the second communication connection comprising a second wired digital connection and/or a second wireless digital connection, the method comprising:
a capturing step of using the image sensors and the sound sensors located in the image capture space to capture images and sounds of the client in the client space thereof, and/or to capture images and sounds of the products in the product space thereof;
a transmitting step of transmitting via the second communication connection the images and the sounds captured in said capturing step to the advisor space;
a displaying step of displaying said images received via the second communication connection on the display means located in the advisor space;
positioning the advisor next to said images displayed on display means located in the advisor space such as to enable the advisor to interact with the images being displayed on display means located in the advisor space, the advisor interacting with the images being displayed either directly or indirectly via pointing means of laser or stick type;

using the sensors provided in the advisor image recapture space to film the advisor in interaction with the displayed images on the display means located in the advisor space to thereby provide real-time recapture images of the advisor in interaction with displayed images on the display means located in the advisor space, wherein the real-time recapture images of the advisor in interaction with displayed images comprise the images displayed on the display means of the advisor space and at least a portion of the body of the advisor in interaction with the images displayed, the recapture images of the advisor in interaction with displayed images not comprising images of the advisor space, or wherein the real-time recapture images of the advisor in interaction with displayed images comprise the images displayed on the display means of the advisor space and the pointing means of the advisor in interaction with the images displayed, the recapture images of the advisor in interaction with displayed images not comprising images of the advisor space; and directly transmitting the provided real-time recapture images of the advisor in interaction with displayed images on the display means located in the advisor space from the advisor image recapture space to the client space via the first communication connection to display said real-time recapture images of the advisor in interaction with displayed images on the display means located in the advisor space on the display means located in the client space, such that the client in real-time sees, in the provided real-time recapture images displayed on the display means located in the client space, the advisor move either in the client space, or in the product space.

2. The method according to claim 1, wherein the client space is identical to the product space.

3. The method according to claim 1, wherein the client space is identical to the image capture space.

4. The method according to claim 1, wherein the client space, the image capture space, and the product space are identical.

5. The method according to claim 1, wherein the product comprises at least one of the following categories:
inert physical products,
living physical products, and
living beings (humans or animals).

6. The method according to claim 1, wherein the client is in direct physical contact with the product or products.

7. The method according to claim 1, wherein the client is in indirect physical contact with the product or products.

8. The method according to claim 1, wherein the image and sound sensors located in the image capture space are mounted on land or maritime flying machines.

9. The method according to claim 1, wherein the client issues, before the operations of the method, a request for provision of instructions and indications regarding design, production, use, utilization, repair, maintenance, consultation, localization, destruction, disposal, localization and elimination, and guidance of one or more products with the advisor.

10. The method according to claim 1, wherein the client makes a search request thereof verbally or in writing in natural, human language on a peripheral unit referred to as client (UPCL1) integrated into the client space and/or into the product space, which client peripheral unit is equipped with:

a module containing artificial intelligence enabling same to interpret and analyze the request of the client (CL1),
sensors enabling same to dialogue and interact:
directly with one or more products (P1 to Pn)
and/or indirectly via the client (CL1), which client being in interaction, in connection (in direct physical contact) with the product or products (P1 to Pn),
at least one video sensor (CVUPCL1) for filming the client (CL1) in interaction, in connection (contact) with the product or products (P1 to Pn),
means for displaying images, videos and technical data of products (P1 to Pn),
which client peripheral unit (UPCL1) identifies the type of product (P1 to Pn), analyses, processes, interprets the request of the client (CL1) and generates the sorting and selection conditions that same sends to at least one central unit referred to as server (SDTC1),
which server central unit (SDTC1) may contain data on the type of products (P1 to Pn) and data on the peripheral units referred to as advisors (UPCO1) with which same is in digital connection and data on the advisor (CO1) or manufacturer (F1), and
which server central unit (SDTC1), after reception of the sorting and selection conditions, selects the type of advisor peripheral unit (UPCO1) capable of responding to the request from the client peripheral unit (UPCL1) and from the client (CL1) such as to make it possible for the advisor peripheral unit (UPCO1) selected to receive the images and/or videos of the client (CL1) in interaction, in connection, in contact with the product or products (P1 to Pn), and which advisor peripheral unit (UPCO1), selected enters into direct connection with a person referred to as advisor (CO1) (expert, specialist in the product and the use thereof) so as to make possible the dialogue between the client (CL1) and the advisor (CO1),
which advisor peripheral unit (UPCO1) is equipped with:
a module containing artificial intelligence enabling same to interpret and analyze the advice of the advisor (CO1),
which advisor (CO1) may communicate verbally or in writing in natural, human language,
sensors enabling same to dialogue and interact with the advisor (CO1),
means for displaying images and/or videos of the client (CL1) in interaction, in connection with the product or products (P1 to Pn), and received from the client peripheral unit (UPCL1) by the advisor peripheral unit (UPCO1),
at least one video sensor for filming the advisor (CO1) in the process of interacting with the images and/or videos of the actual client (CL1) in interaction (in connection/in contact) with the product or products (P1 to Pn),
which images and/or videos of the advisor (CO1) in interaction with the images or videos of the client (CL1) are sent back to the client peripheral unit (UPCL1) and displayed on the display means equipping the client peripheral unit (UPCL1) such that the client (CL1) sees the image thereof or videos superimposed with the image or the video of the advisor (CO1) in the process of giving same the analysis and the technical expertise.

11. The method according to claim 10, wherein the client peripheral unit (UPCL1) communicates directly with the advisor peripheral unit (UPCO1) without passing through the central unit referred to as server (SDTC1).

12. The method according to claim 10, wherein the advisor peripheral unit (Co1) enters into relation with other advisor peripheral units (CO1, UPF1) via or not one or more intermediate servers.

13. The method according to claim 10, wherein the advisor (CO1 or F1) is in interaction (in connection/in contact) with other products (P1 to Pn), which products are in interaction (in connection/in contact) with the advisor peripheral unit (UPCO1, UPF1).

14. The method according to claim 10, wherein the client peripheral unit (UPCL1) and the client (CL1) that uses same are located in a physical store for selling products (P1 to Pn).

15. The method according to claim 10, wherein the products (P1 to Pn) are clothes.

16. The method according to claim 10, wherein the products (P1 to Pn) are mutually in connection.

17. The method according to claim 10, wherein the products (P1 to Pn) are equipped with means for the recognition thereof or the identification thereof by the peripheral unit (UPCL1).

18. The method according to claim 10, wherein each of the advisor or client spaces is fixed or mobile.

19. The method according to claim 10, wherein the method is applied in at least one of the following situations of request for advice or for assistance:
   request for advice for the purchase of a product by communication of the client with a specialist advisor,
   request for advice for a health condition by communication between a patient and a medical advisor,
   request for advice for a health condition by communication between a patient caregiver and a medical advisor,
   request for remote dispensing of medicinal products by communication between a patient and a chemist and/or a doctor,
   request for advice for the maintenance of a product by communication between a user of the product and a specialist of said latter,
   request for assistance in the driving of a vehicle by communication between a passenger or a driver of the vehicle with a specialist of said driving,
   request for assistance on a military operations site between a soldier and a military advisor.

20. A communication device for implementing the method according to claim 10, further comprising at least one client peripheral unit (UPCL1) made available to the client (CL1) and comprising:
   a module containing artificial intelligence enabling same to interpret and analyze the request of the client (CL1),
   sensors enabling same to dialogue and interact:
   directly with one or more products (P1 to Pn),
   and/or indirectly via the client (CL1), which person being in interaction, in connection (in direct physical contact) with the product or products (P1 to Pn),
   at least one video sensor (CVUPCL1) for filming the client (CL1) in interaction (in connection/in contact) with the product or products (P1 to Pn),
   means for displaying images, videos and technical data of products (P1 to Pn),
   means for displaying images and/or videos of the advisor (CO1, F1) in interaction with the images or videos of the actual client (CL1) in interaction with the product or products (P1 to Pn) such that the client (CL1) sees the image thereof or videos superimposed with the image or the video of the advisor (CO1, F1) in the process of giving same the analysis thereof and/or the technical expertise on the product or products (P1 to Pn),
   a server central unit (SDTC1) that selects the type of advisor peripheral unit (UPCO1, UPF1) according to the sorting and selection orders received from the client peripheral unit (UPCL1),
   at least one other peripheral unit (UPCO1, UPF1) referred to as advisor made available to an advisor (CO1, F1) including:
   a module containing artificial intelligence making it possible for same to interpret and analyze the advice of the advisor (CO1, F1), which advisor communicates verbally or in writing in natural, human language,
   sensors enabling same to dialogue and interact with the advisor (CO1, F1),
   means for displaying images and/or videos of the client (CL1) in interaction with the product or products (P1 to Pn), and received from the client peripheral unit (UPCL1) by the advisor peripheral unit (UPCO1),
   at least one video sensor for filming the advisor (CO1, F1) in the process of interacting with the images and/or videos of the actual client (CL1) in interaction with the product or products (P1 to Pn),
   which images and/or videos of the advisor (CO1, F1) in interaction with the images or videos of the client (CL1) are sent back to the client peripheral unit (UPCL1) and displayed on the display means equipping the client peripheral unit (UPCL1) such that the client (CL1) sees the image thereof or videos superimposed with the image or the video of the advisor (CO1, F1) in the process of giving same the analysis and the technical expertise.

21. The device according to claim 20, wherein the product (P1) is a patient, the client (C11) is a doctor or a nurse/requester of advice and the advisor (CO1) is an expert doctor.

22. The device according to claim 20, wherein the product (P1) consists of measurement means (body temperatures, blood pressure, heart beats, etc.), the client (CL1) is a patient and the advisor (CO1) is an expert doctor.

23. The device according to claim 20, wherein the product (P1) is a medicinal product, the client (CL1) is a patient, the advisor or advisors (CO1) are a doctor and/or a chemist.

24. The device according to claim 20, wherein the product (P1) is an item of equipment, a product, an infrastructure, the client (CL1) is a repair maintenance operator and the advisor (CO1) is an expert in said equipment, product, infrastructure.

25. The device according to claim 20, wherein the product (P1) is a vehicle wherein is found the client (C11), the advisor (CO1) is an expert of said vehicle and/or of the environment wherein said vehicle (P1) moves.

26. The device according to claim 20, wherein the client peripheral unit (UPCL1) is a means for distributing products supplied as products by a locked product storage area and not accessible for the client (CL1), the distribution of products requiring beforehand the dialogue between client (CL1) and advisor (CO1, F1) and the authorization of the advisor (CO1, F1).

27. The device according to claim 20, wherein the camera is equipped with a correction means comprising a bifocal focus lens (700), which lens consists of two half-lenses (710, 720) (symmetrical or not) of different dioptries or of different magnifications and the gluing (assembly) axis of which is located in a plane perpendicular to the axis of the lens of the camera.

28. The device according to claim 27, wherein the lens is provided with a means for rotating the lens about the means for rotating at 360° or for moving from left to right so as to make move from left to right or from right to left the assembly axis of the two half-lenses.

29. The device according to claim 27, wherein the correction means consists of a half-lens of a dioptry or of a magnification other than the air, the other half being the free air.

30. The device according to claim 27, wherein the correction means consists of a progressive lens of a dioptry or of a magnification varying from left to right increasingly or decreasingly for an observer facing a lens of an advisor camera.

* * * * *